United States Patent [19]
van den Bergh et al.

[11] Patent Number: 5,695,583
[45] Date of Patent: Dec. 9, 1997

[54] LIGHT DIFFUSER AND PROCESS FOR THE MANUFACTURING OF A LIGHT DIFFUSER

[75] Inventors: Hubert van den Bergh, Goumoens-la-Ville; Jérôme Mizeret, Cossonay, both of Switzerland

[73] Assignee: Novartis Corporation, Summit, N.J.

[21] Appl. No.: 593,312

[22] Filed: Jan. 31, 1996

Related U.S. Application Data

[62] Division of Ser. No. 413,815, Mar. 17, 1995, Pat. No. 5,536,265.

[30] Foreign Application Priority Data

Mar. 25, 1994 [EP] European Pat. Off. ............ 94810188

[51] Int. Cl.$^6$ ...................... B32B 31/00; B05D 5/06
[52] U.S. Cl. ................ 156/153; 156/285; 156/294; 156/305; 427/163.2; 427/212; 427/385.5; 427/407.1; 427/407.2; 427/389.7; 427/389.8
[58] Field of Search ................ 427/163.2, 212, 427/385.5, 407.1, 407.2, 389.7, 389.8; 156/99, 166, 294, 305, 285, 153

[56] References Cited

U.S. PATENT DOCUMENTS

| | | | |
|---|---|---|---|
| 4,017,150 | 4/1977 | Imai | 350/96 BC |
| 4,311,142 | 1/1982 | Machida | 128/303.1 |
| 4,336,809 | 6/1982 | Clark | 128/665 |
| 4,445,892 | 5/1984 | Hussin et al. | 604/101 |
| 4,551,129 | 11/1985 | Coleman et al. | 604/21 |
| 4,558,093 | 12/1985 | Hatzenbuhler | 524/837 |
| 4,660,925 | 4/1987 | McCaughan, Jr. | 350/96.15 |
| 4,693,244 | 9/1987 | Daikuzono | 128/303.1 |
| 4,693,556 | 9/1987 | McCaughan, Jr. | 350/320 |
| 4,736,743 | 4/1988 | Daikuzono | 128/303.1 |
| 4,842,390 | 6/1989 | Sottini et al. | 350/96.15 |
| 4,860,743 | 8/1989 | Abela | 128/303.1 |
| 4,913,142 | 4/1990 | Kittrell | 606/7 |
| 4,916,247 | 4/1990 | Steinmann | 556/82 |
| 4,927,231 | 5/1990 | Levatter | 350/96.32 |
| 4,927,426 | 5/1990 | Dretler | 606/128 |
| 5,054,867 | 10/1991 | Wagnieres et al. | 385/31 |
| 5,071,417 | 12/1991 | Sinefsky | 606/8 |
| 5,151,096 | 9/1992 | Khoury | 606/15 |
| 5,209,748 | 5/1993 | Daikuzono | 606/16 |
| 5,219,346 | 6/1993 | Wagnieres et al. | 606/16 |
| 5,401,270 | 3/1995 | Muller et al. | 606/13 |
| 5,415,655 | 5/1995 | Fuller et al. | 606/16 |
| 5,431,647 | 7/1995 | Purcell, Jr. et al. | 606/16 |

FOREIGN PATENT DOCUMENTS

| | | |
|---|---|---|
| 0292621 | 11/1988 | European Pat. Off. . |
| 0450149 | 10/1991 | European Pat. Off. . |
| 0500960 | 9/1992 | European Pat. Off. . |
| 2154761 | 9/1985 | United Kingdom . |
| 9204648 | 3/1992 | WIPO . |

OTHER PUBLICATIONS

Merck Index—11th Edition 1989 pp. 1207 and CL 286. (No Mo.).

Wagnieres et al. "Photodynamic Therapy of Early Cancer in the Upper Aerodigestive Tract and Bronchi; Instrumentation and Clinical Results." SPIE Institute Series vol. 1S 6 (1990) pp. 249–264. (No Mo).

*Primary Examiner*—Janyce Bell
*Attorney, Agent, or Firm*—Gregory D. Ferraro

[57] ABSTRACT

A light diffuser for the radial emission of light, which has been fed into the diffuser in axial direction, comprises an optical waveguide, which itself comprises a core and a cladding. The core of the waveguide is exposed at an active region at the distal end. The exposed active region of the core is optically separated from a substance containing scattering particles. In a preferred embodiment, the core is roughened and is embedded in a first layer of an elastic substance, which has a refractive index similar to the refractive index of the cladding and which does not contain any scattering particles. This first layer is embedded in at least one further, second layer of an elastic substance comprising the scattering particles. This substance is surrounded by the outer tube.

9 Claims, 4 Drawing Sheets

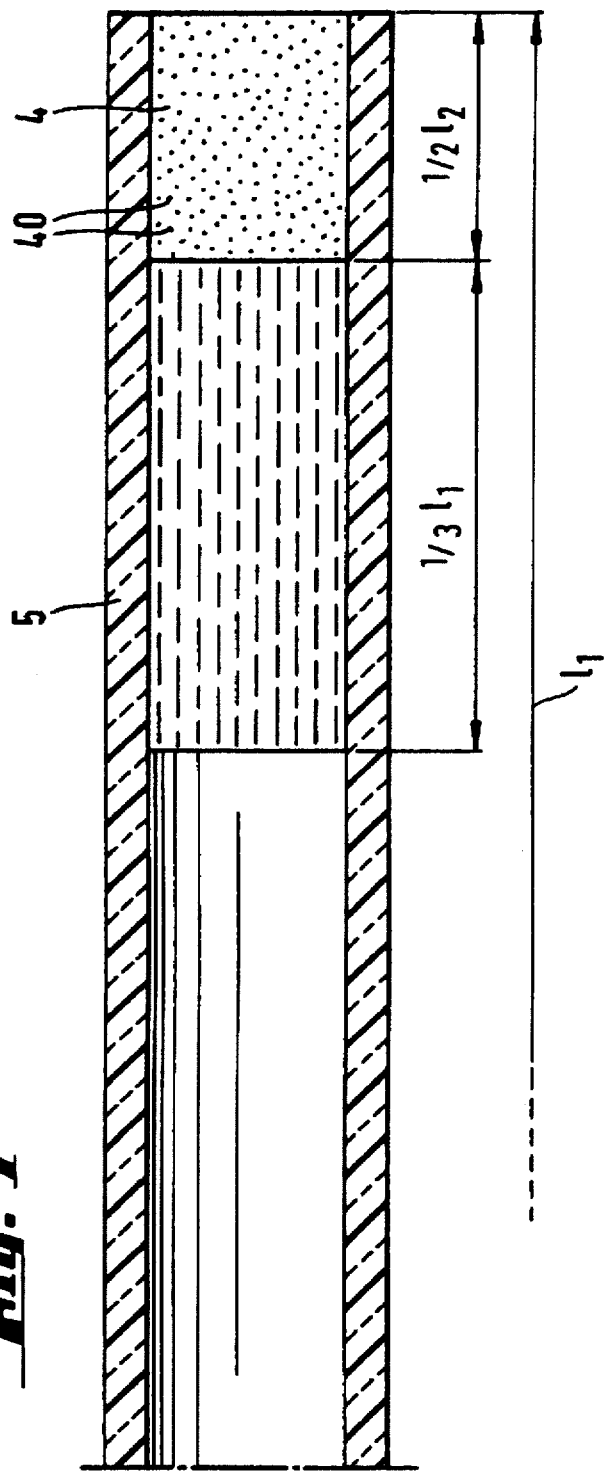
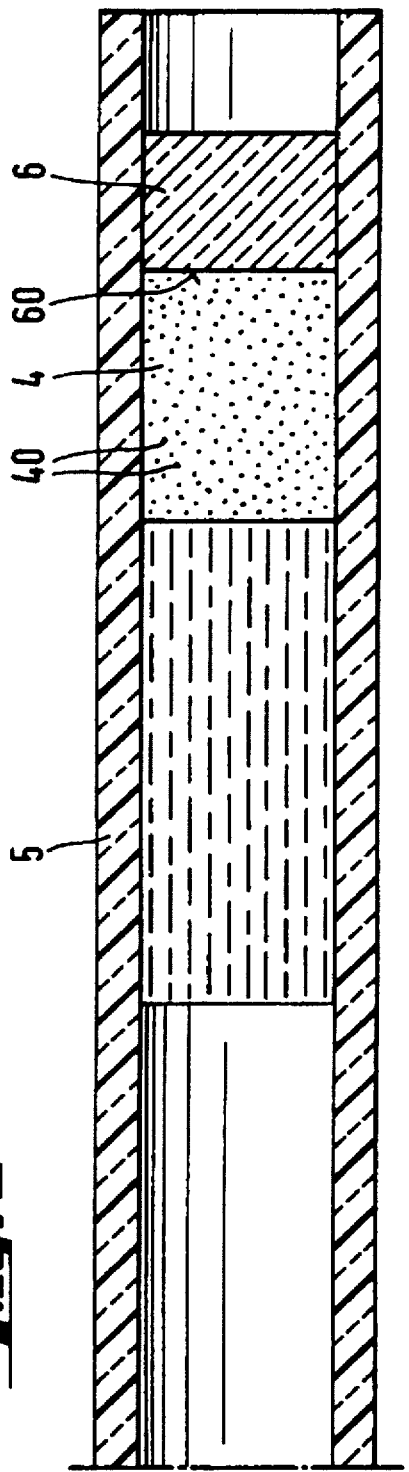

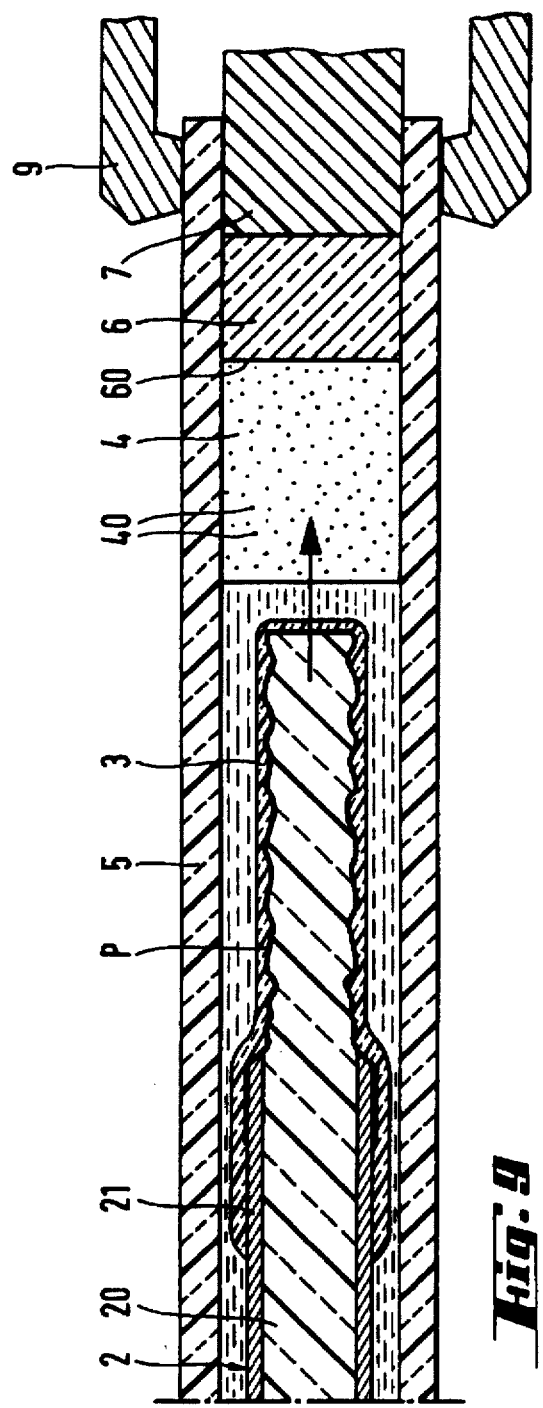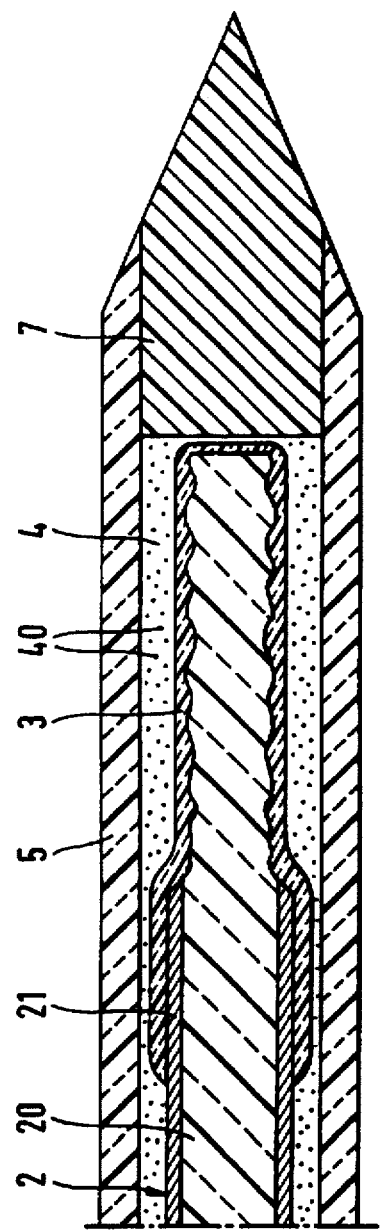

LIGHT DIFFUSER AND PROCESS FOR THE MANUFACTURING OF A LIGHT DIFFUSER

This is a division of Ser. No. 08/413,815, filed Mar. 17, 1995, now U.S. Pat. No. 5,536,265.

This invention relates to a light diffuser and to a process for the manufacturing of a light diffuser according to the preamble of the respective independent patent claim.

Light diffusers, which do radially emit light, which has been fed into the diffusers axially, are well-known in the art especially in the field of photodynamic therapy (PDT). Several of such light diffusers used in interstitial PDT-treatments as well as in PDT of the hollow organs—for instance the upper aerodigestive tract, the traebco-bronchial tree or the esophagus—are based on frontal coupling of the light beam into a scattering medium. That is to say, the light is emitted from an optical waveguide, into which the light has been fed from a light source or from a special assembly for feeding into the waveguide, in axial direction into a scattering medium or into a medium containing scattering particles. This kind of frontal coupling is known, for example, from EP-A-0 437 183. Another way of coupling the light into the scattering medium is known, for example, from U.S. Pat. No. 5,151,096. In the diffuser disclosed there, the coupling of light into the scattering medium is performed in such a way, that the core of the waveguide is exposed at its distal end and the exposed end of the core is embedded in a substance containing the scattering particles. The substance containing the scattering particles is surrounded by an outer tubular sleeve being provided with a tip for easy penetration of cancerous tumors.

One of the major inconveniencies of frontal coupling is, that the concentration of the scattering particles contained in the scattering medium generally is not constant. It is normally made to increase with the distance traversed through the scattering medium in order to achieve a homogeneous light intensity distribution in the tissue near the surface, where the light is emitted radially from the diffuser. This increasing concentration of light scattering particles compensates for loss of intensity of non-scattered light along the main cylindrical axis due to the light scattering. Other desired intensity profiles can be achieved by varying the local concentration of scattering particles in the scattering medium in an appropriate way. Precise inhomogeneous scattering particle concentration profiles, however, can be very difficult to manufacture. Hence, this problem has been overcome, for instance, by providing a number of separate scattering zones, typically three to five zones, each of which has a different scattering particle concentration.

This is in fact one possible solution of the problem how to overcome the difficult manufacture of an inhomogenous particle concentration profile. However, several different zones of particle concentrations still imply a relatively high expense in the manufacture of such diffusers. Additionally, although a relatively homogeneous distribution can be achieved, there is still some potential to improve homogeneity of the light intensity distribution along the main cylindrical axis of the diffuser. A further disadvantage of known diffusers is, that all of the scattering particles contained in the scattering medium are located directly in the path of the main light beam in the diffuser, so that they may absorb a certain amount of the light. This can lead to a strong local heating, which may cause damage to the diffuser.

Another type of diffuser with radial coupling is known as being prior art. These diffusers are made from optical fibers with a silica core and a surrounding layer made from acrylate polymer (having the same refractive index as the core) loaded with scattering particles. One of the major inconveniencies of such radial coupling diffusers is, that the silica core has to be stripped and therefore exposed to ambient air. This operation makes the diffusing region extremely fragile. Another inconvenience of this kind of diffuser is that the light travels in the medium containing the scattering particles and therefore the amount of light coupled to the outside decreases with the distance along the axis of the diffuser if the particle concentration is left constant. In addition, since the light travels through the layer containing the scattering particles thus creating the possibility of local heating and damage.

It is therefore an object of the instant invention to suggest a diffuser and a process for manufacturing such a diffuser, which overcome the aforementioned disadvantages of the prior art.

With respect to the diffuser according to the instant invention, the above mentioned disadvantages of prior art diffusers are overcome by optically separating the core from the substance containing the scattering particles and keeping the core separated from the substance containing the scattering particles up to the distal end of the active region. Such a diffuser allows the light to travel in a medium which is optically clear up to the distal end of the diffuser. The scattering medium is separated (radially) and optically isolated from the medium in which the light propagates. In a preferred embodiment this is achieved by roughening an exposed active region at the distal end of the core and embedding it in a first layer of an elastic substance, which has a refractive index similar to that of the cladding and which does not contain any scattering particles. This first layer is embedded in at least one further, second layer of an elastic substance comprising the scattering particles, which itself is surrounded by the outer tube. Since the materials used for the different layers are elastic, they do not render the diffuser extremely fragile and therefore such a diffuser is suitable among others for interstitial PDT. Furthermore, since no scattering particles are located either directly in the path of light or in direct contact with, or close to, the outer surface of the core, no significant local heating occurs and accordingly damage of the diffuser, which could have resulted from such local heating, is avoided.

An important advantage results from the fact, that no scattering particles are located in direct contact with the outer surface of the core: A large fraction of the light propagating in the core is reflected at the outer surface of the core and thus keeps on propagating in the core, i.e. does not emerge through the outer surface of the core. Even the evanescent wave, that part of light reflected at the core surface which slightly penetrates the thin layer covering the core, does essentially not come into contact with the layer containing the scattering particles. That part of light emerging through the outer surface of the core, which is subsequently scattered by the scattering particles, can be controlled by changing the roughness of the core. Since it is only a relatively small part of the light, which emerges through the outer surface of the core, according to a further aspect of the instant invention it is possible, by varying the surface roughness of the core along the axial direction, to achieve a homogeneous intensity distribution of light. By providing a layer containing a homogeneous concentration (at least in axial direction) of scattering particles, the light leaving the core which is forward directed (i.e. in the direction of light propagation in the core) is finally rendered omnidirectional.

According to a further advantageous embodiment, a mirror is provided at the distal end of the diffuser for reflecting the light emerging from the waveguide in axial direction. Accordingly, the light emerging through the end face of the optical waveguide is reflected at the mirror and is then propagating back through the waveguide in the reverse direction. Parts of this reflected light are again emerging through the outer surface of the core and are subsequently scattered by the scattering particles. By means of the mirror a greater part of the light fed into the proximal end of the diffuser is used for the irradiation and the degree of homogeneity of the light distribution along the main cylindrical axis of the diffuser is further improved.

In order to effectively close and stabilize the distal end of the diffuser, a terminating stopper can be provided at the distal end of the outer tube in accordance with a further embodiment of the diffuser according to the invention. Such stopper can have the form of a sharp tip in order to simplify the introduction of the diffuser into the tissue in interstitial PDT-treatment.

According to a further embodiment of the diffuser according to the invention, the diameter of the core of the waveguide is in the range of from about 250 μm to about 3000 μm, in particular from about 500 μm to about 750 μm. Such diameters of the core allow light energies up to 4 Watts to be fed into the core with a very low probability of causing damage to the diffuser. The inner diameter of the outer tube is about 100 μm larger than the diameter of the core of the waveguide, and the outer diameter of the outer tube is in the case of core diameters of from about 500 μm to about 750 μm from about 0.9 mm to about 1.2 mm. Significantly smaller diameters can also be attained. Accordingly, the outer dimensions of the whole diffuser are relatively small while allowing at the same time high light energies to be fed into the diffuser.

Practical embodiments of the diffuser according to the present invention have an exposed active region having a length of up to about 100 mm, which is embedded in the elastic substance. However, depending on the respective application of the diffuser, the respective length of the exposed core can also be outside of this range of lengths.

As an example for materials or substances, which can be used for the several parts of the diffuser, the core of the waveguide can be made from polymethylmethacrylate. The cladding of the waveguide can be made from a fluorinated polymer and the elastic substance can be silicone. The scattering particles can be $TiO_2$-particles having a diameter of about 200 nm. The outer tube can be made from polyamide, from polytetrafluoroethylene or from polypropylene.

In order to achieve a simple and reliable handling of the diffuser, a further advantageous embodiment of the diffuser can be provided with a connector at its proximal end, which is adapted to be connected to a respective counterpart at an assembly for feeding light into the diffuser. Thus, the user of such a diffuser needs only to plug the connector into the respective counterpart of an assembly for feeding light into the waveguide of the diffuser and the diffuser is immediately ready for use. This may be especially interesting for applications in a sterile atmosphere, since no specific adjustments have to be made, only the connector has to be plugged into the respective counterpart in order to make the diffuser ready for use.

With respect to a process for manufacturing such diffusers, the end face of an optical waveguide, which comprises a core and a cladding, is polished at its distal end. The cladding is removed in the active region near the distal end of the waveguide thereby exposing the core. The exposed active region is roughened and is then embedded in a first layer of an elastic substance, which has a refractive index similar to the refractive index of the cladding and which does not contain any scattering particles. The thus embedded active region is subsequently embedded in at least one further, second layer of an elastic substance, which contains scattering particles. Finally, the outer tube is employed around this layer. Such process allows an easy and reliable manufacture of the diffuser according to the present invention.

In a preferred and practical modification of the manufacturing process according to the present invention, in order to embed the active region, a polymerizable, fluid medium, which is at least partially not yet polymerized, is applied to the core in the active region. The medium adhering to the core is then polymerized and thus the first layer embedding the core is produced. Subsequently, further polymerizable, fluid medium, which is at least partially not yet polymerized and which does not contain any scattering particles, is sucked through the distal end into the outer tube. Thereafter, further polymerizable fluid medium, which is at least partially not yet polymerized but contains scattering particles, is sucked through the distal end into the outer tube. Then a terminating stopper is introduced at the distal end of the outer tube and finally the waveguide is introduced through the proximal end of the outer robe into the outer tube. The introduction of the waveguide is performed in such a way, that the active region, which is embedded, is forwarded through the outer tube until it is located in the medium containing the scattering particles. Finally, the polymerizable media are polymerized.

In a further modification of the process according to the invention, prior to the introduction of the terminating stopper a mirror is introduced through the distal end into the outer tube. The advantages resulting from the provision of a mirror at the distal end of the diffuser are already discussed above.

According to a further modification of the process concerning the present invention, prior to the embedding of the exposed active region a primer is applied to the core in the active region in order to improve the adhering properties of the roughened core and to allow the elastic medium to adhere well to the core.

In accordance with a further modification of the process, a waveguide having a core with a diameter in the range of from about 250 μm to about 3000 μm is introduced into the outer tube. Particularly, a core having a diameter in the range of from about 500 μm to about 750 μm is introduced into the outer tube. The outer tube has an inner diameter which is about 100 μm larger than the outer diameter of the core of the waveguide, the outer diameter of the outer tube being in the range from about 0.9 mm to about 1.2 mm for core diameters in the range of from 500 μm to 750 μm. The advantages resulting from the special election of these dimensions have already been discussed with respect to the diffuser.

The same applies to that modification of the process in which the length of the active region of the waveguide, which is exposed, is chosen up to about 100 mm and to that modification of the process, in which a waveguide is used, which has a core made from polymethylmethacrylate and a cladding made from a fluorinated polymer. For example, the elastic substance is silicone, the scattering particles are $TiO_2$-particles having a diameter of about 200 nm, and the outer tube is made from polyamide, polytetrafluoroethylene or polypropylene. Other similar substances or particles can also be used.

In a further modification of the process, a connector is provided at the proximal end of the waveguide, the connector being connected in use to a respective counterpart in an assembly for feeding light into the waveguide. Again, the advantages resulting therefrom have already been discussed with respect to the corresponding embodiment of the diffuser.

BREIF DESCRIPTION OF DRAWINGS

FIGS. 4, 5, 6, 7, 8, 9 and 10 show an example of different steps of the process for manufacturing the diffuser.

Figure 1:
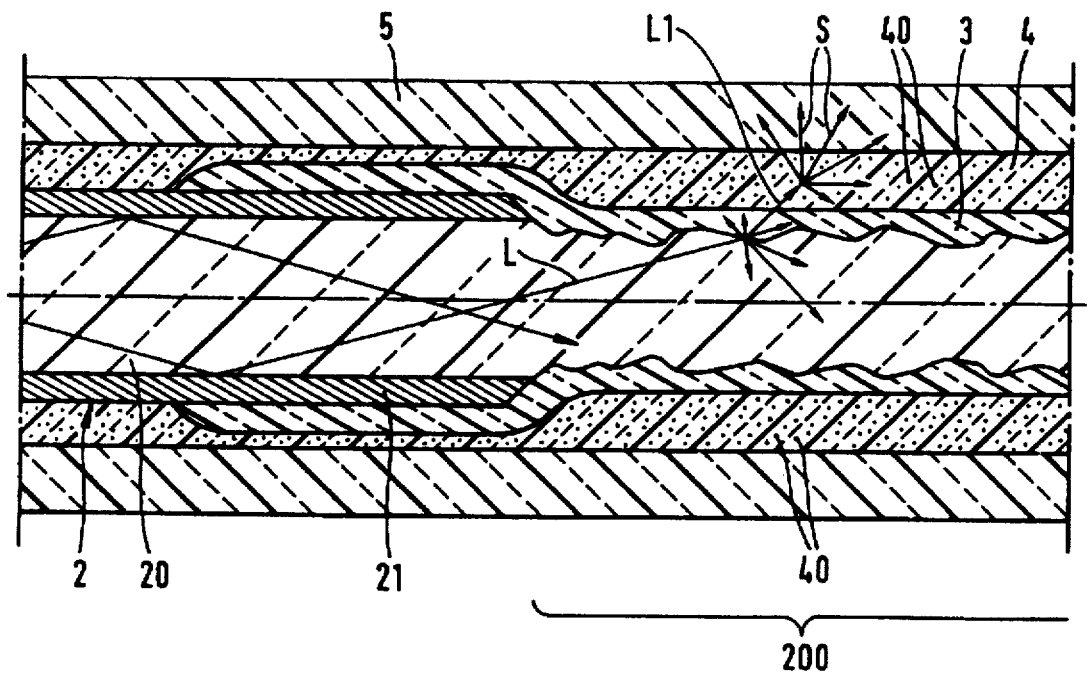
FIG. 1 shows an embodiment of the most essential parts of a diffuser according to the instant invention.
Figure 2:
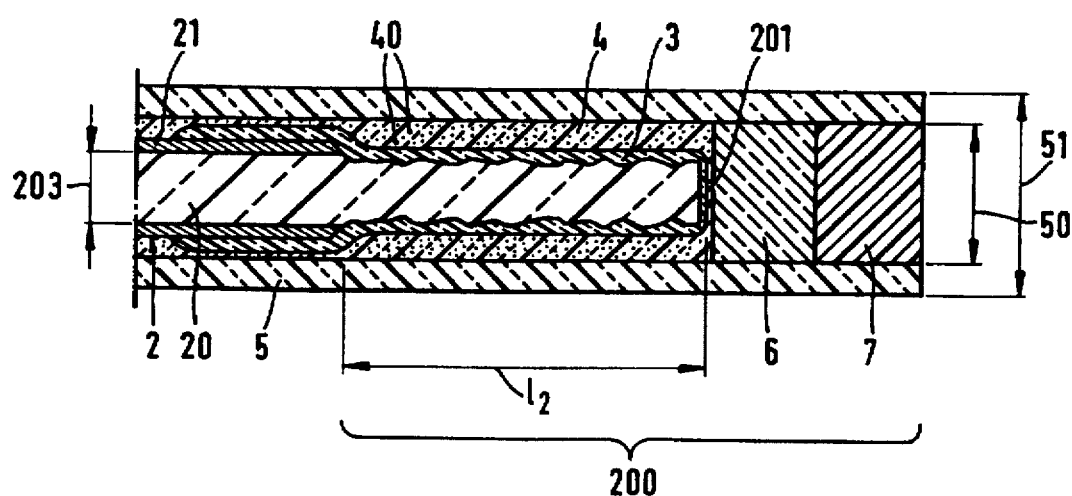
FIG. 2 shows the embodiment of FIG. 1, which is additionally provided with a mirror and terminating stopper.
Figure 3:
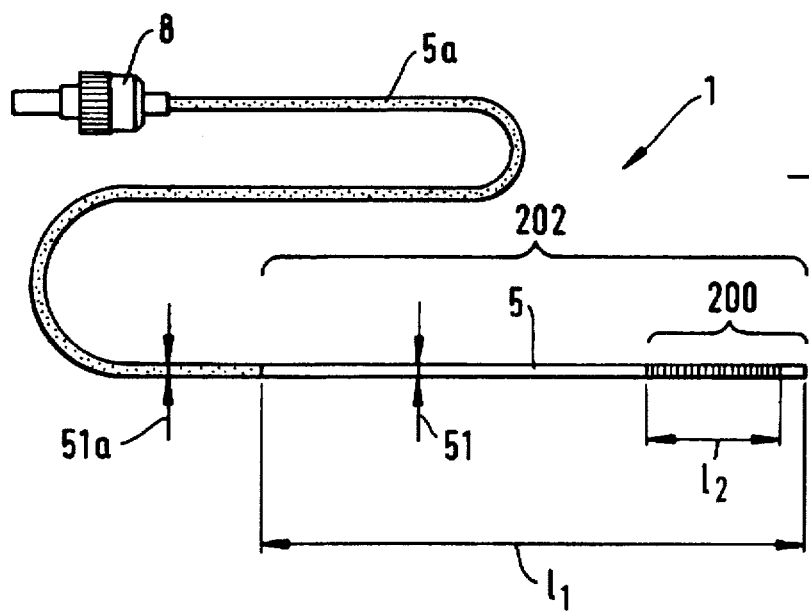
FIG. 3 shows a complete diffuser being provided with a connector.

The invention will be explained in more detail below by means of the accompanied drawing, in which:

FIG. 1 shows an embodiment of the most essential parts of a diffuser according to the instant invention, FIG. 2 shows the embodiment of FIG. 1, which is additionally provided with a mirror and a terminating stopper, FIG. 3 shows a complete diffuser being provided with a connector, and FIGS. 4, 5, 6, 7, 8, 9 and 10 show an example of different steps of the process for manufacturing the diffuser.

According to FIG. 1 the essential parts of an embodiment of the whole diffuser 1, which is represented in FIG. 3, comprise an optical waveguide 2 having a core 20 and a cladding 21. The core 20 is exposed and roughened in an active region 200 near its distal end 201. The exposed active region 200 near the distal end 201 of the core 20 is embedded in a first layer 3 of an elastic substance, which does not contain any scattering particles. The first layer 3 is embedded in a second layer 4 of an elastic substance, which contains scattering particles 40. This second layer 4 is then surrounded by an outer tube 5. Concerning the propagation and the scattering of the different light rays also represented in FIG. 1, the way how the diffuser works will be explained in more detail later.

In FIG. 2 the embodiment of the diffuser represented in FIG. 1 is shown again, but additionally the embodiment shown here is provided with a mirror 6 and with a terminating stopper 7 at its distal end.

FIG. 3 shows an embodiment of the whole diffuser 1, which is provided with a connector 8 at its proximal end. The connector 8 can be plugged into a respective counterpart of an assembly (not shown) for feeding light into the diffuser 1. The diffuser 1 according to this embodiment is further provided with an additional essentially non-transparent protective outer tube 5a extending from the proximal end to a region 202 near the active region 200 at the distal end 201 of the waveguide. At its distal end it can be glued to outer tube 5. The overall length of the diffuser can, for instance, be about two meters, whereas the length of the region 200 can, for instance, be about 200 mm. The exposed active region 200 near the distal end 201 can have a length of about 25 mm to about 100 mm. Depending on the respective PDT-application, the length $l_2$ of the active region 200 can of course be varied outside of this range.

The waveguide 2 can, for example, be an optical fiber available from Toray Industries (Japan), the core being made from polymethylmethacrylate with a refractive index of n=1.492 and a cladding made from a fluorinated polymer with a refractive index of n=1.419. The numerical aperture of this fiber is NA=0.46 corresponding to an acceptance angle of about 55°. These fibers have an attenuation of about $\alpha$=0.13 dB/m at a wavelength of $\lambda$=514.5 nm, an attenuation of about $\alpha$=0.47 dB/m at a wavelength of $\lambda$=630 nm, and an attenuation of about $\alpha$=0.15 dB/m at a wavelength of $\lambda$=652 nm. The elastic substance of the first layer 3 can be Rhodorsil® RTV 141, a silicone elastomer comprising a resin and a hardener. The elastomer has a refractive index of n=1.406 after polymerization and is available from Rhône Poulenc. This substance is essentially transparent at all wavelengths of interest. The substance of the second layer 4 can also be a silicone elastomer, however, this second layer 4 contains scattering particles. These scattering particles can, for example, be $TiO_2$-particles having a diameter of about 200 nm. The outer tube 5 can be made from Polytetranfluoroethylene (PTFE) having a refractive index of n=1.35 or from polyamide having a refractive index of n=1.51. Polypropylene having a refractive index of n=1.49 is another alternative for the material from which the outer tube 5 can be made.

The core 20 of the waveguide 2 in this particular case has a diameter 203 of about 500 μm to about 750 μm, but can be selected both to be significantly larger or smaller. In the embodiment shown in FIG. 2, the core has a diameter 203 of 500 μm. The inner diameter 50 of outer tube 5 is about 100 μm larger than the diameter of the core 20. The outer diameter 51 of outer tube 5 in this particular case is in the range from 0.9 mm to 1.2 mm, but can be selected both to be larger or smaller depending on the diameter of the core 20. In the embodiment shown in FIG. 2, the outer diameter 51 of outer tube 5 is about 0.9 mm. The additional protective outer tube 5a of the described embodiment has an outer diameter 51a of 1 mm. At the proximal end of diffuser 1 a connector 8 (FIG. 3) is provided, which can be any suitable connector, which can easily be plugged into a respective counterpart of an assembly (not shown) for feeding light into diffuser 1.

Returning now to FIG. 1, in operation light L fed into the diffuser 1 or waveguide 2, respectively, propagates through the core 20 and subsequently reaches the embedded active region 200, in which the exposed core is roughened. Since active region 200 is embedded in the first layer 3 of an elastic substance, which does not contain any scattering particles, and since the refractive index of first layer 3 is less than that of the core 20, light would normally not emerge through the radial outer surface of the corn 20. However, since in active region 200 the core is roughened, a small part of the light emerges through the outer surface of the core 20. That pan L1 of light, which emerges through the outer surface of core 20 can be influenced by the degree of roughening—the more coarse the toughening of the core, the more light emerging through the radial outer surface.

In the described embodiment, only a small part L1 of the light emerges through the radial outer surface. Most of the light is reflected and therefore further propagates in core 20. The light L1, which has emerged through the outer surface, is emitted in several directions, in the described embodiment it has an intensity maximum at an angle of about 45° with respect to the main cylindrical axis. Since there are no scattering particles contained in the first layer 3, the light cannot be scattered and passes straight through this layer. A great advantage resulting therefrom is, that since no scattering particles are located in direct contact with the outer surface of core 20, no significant local heating may occur and accordingly damage of the diffuser, which could have resulted from such local heating, is avoided. Layer 3 thus acts as an optical spacer.

The light L1, which has passed through layer 3 then reaches second layer 4, which contains scattering particles 40. When striking the particles 40 the light is scattered isotropically, as indicated by arrows S. Since the distribution of the particles 40 in second layer 4 is homogeneous at least in the direction of the main cylindrical axis (as well as in 360° around the cylinder), the radial emission of light (around the cylinder) is very homogeneous.

The light, which has been reflected at the radial outer surface of the core 20 finally emerges through the end face at the distal end 201 of waveguide 2 and strikes mirror 6, where it is reflected and propagates through core 20 in the reverse direction. When the light strikes the radial outer surface of core 20, a pan of the light again emerges through the radial outer surface of core 20, and the main pan is reflected and propagates in reverse direction in the core 20.

In some applications it may be desirable, that light emerges also axially, i.e. in the direction of the main cylindrical axis. In such applications the mirror 6 is omitted. It can also be desirable to manufacture for instance 180°-diffusers, which radially emit light only over an angle of 180°. In order to achieve this, at the radial outer surface a reflecting surface or coating may be provided. All the above described diffusers are suitable for various types of PDT-applications, especially for interstitial PDT-treatment, wherein such a diffuser can be introduced at the desired location for instance via a hypodermic needle.

An additional advantage of the diffuser according to the present invention is, that it is both robust and flexible with a possible radius of curvature of the order of 10 mm. Furthermore, it is not very sensitive to heat shock or chemical attack, so that it can be easily sterilized after use.

Figure 4:
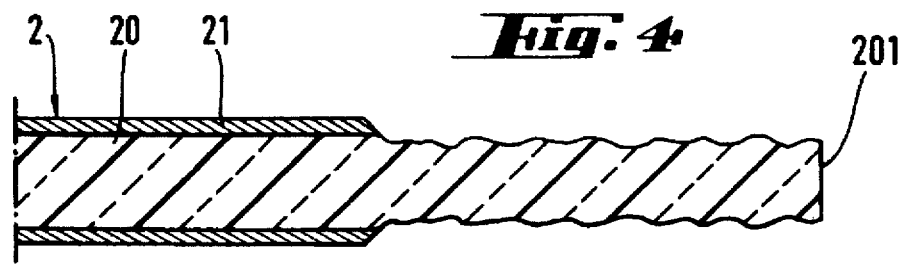
Figure 5:
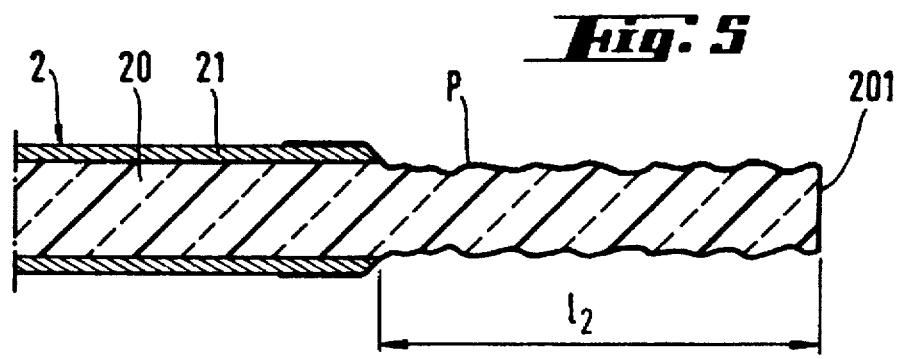

An example for the process for manufacturing a diffuser is illustrated by means of FIG. 4–10, which represent the single steps to be performed in order to manufacture the diffuser. At the beginning the end surface of waveguide 2, which can be the aforementioned waveguide with a PMMA-core and a refractive index of n=1.492 and a cladding made from a fluorinated polymer with a refractive index of n=1.419, available from Toray industries in various diameters, is polished down to a grain of, for instance, 0.3 μm (not shown). Then, cladding 21 is removed from core 20 thereby exposing the active region 200 at the distal end 201 of core 20. Active region 200 is removed and at the same time roughened. This removal of cladding 21 and toughening of core 20 can be done, for instance, by using specific sandpaper for optical polishing with a suitable solvent, for instance a mixture of $H_2O$ and ethanol in a 2:1 ratio. A thus toughened core 20 is shown in FIG. 4.

After having finished the toughening, a primer P is applied over the whole length $l_2$ of the active region 200 to exposed core 20 (FIG. 5) in order to increase the adherence of the silicone elastomer. The solvent for the primer may be methanol. The applied primer is then left to dry for about half an hour.

Figure 6:
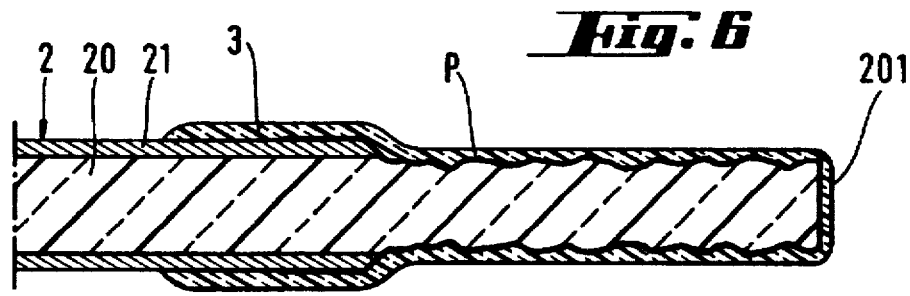

The next step is to apply a thin layer of silicone elastomer (resin plus hardener), the thickness of which is typically about 10 to 20 μm, to the core 20 (FIG. 6). The applied silicone elastomer has been degassed prior to its application to core 20. After having applied the elastomer, polymerization is initiated with waveguide 2 being positioned with its distal end 201 up in order to allow excess elastomer to flow away.

The step following next (FIG. 7) is to introduce liquid silicone elastomer (resin plus hardener, without scattering particles) over a length of for instance ⅓ of the length $l_1$ of region 202 over which outer robe 5 extends into outer tube 5. The latter can be made from PTFE or other materials already mentioned. The introduction of liquid silicone elastomer can, for instance, be performed by applying suction to the proximal end. After having sucked in the pure liquid elastomer, silicone elastomer (resin plus hardener) loaded with scattering $TiO_2$-particles having a diameter of about 200 nm is then sucked into outer robe 5 over a length of for instance ½ of the length $l_2$ of active region 200. In addition to the $TiO_2$-particles the silicone can be loaded with some $Al_2O_3$-particles having a diameter of about 10–30 μm. The concentration of $TiO_2$-particles can be of the order of 1–5% by weight, the concentration of $Al_2O_3$-particles is at least a factor 10 less than the concentration of $TiO_2$-particles. The main purpose of the $Al_2O_3$-particles is to act as a spacer between the embedded core and the outer robe 5, so that core 20 is centered in outer tube 5.

Depending on whether or not an axial emission of light is also desired mirror 6 is then introduced into outer tube 5 from the distal end with its reflecting surface 60 facing towards the proximal end (FIG. 8). The reflecting surface 60 of mirror 6 can be coated with a thin layer of primer for better adherence. It is pushed sufficiently far into outer tube 5 to leave room for a stopper.

In the step following next (FIG. 9), terminating stopper 7 is then introduced into outer robe 5 and is pushed forward until it contacts mirror 6, and is then held in place with a clamp 9. Thereafter, the waveguide 2 is introduced through the proximal end into outer tube 5, the embedded active region being forwarded through outer tube 5 until it is located in the silicone containing the particles, especially until it touches the reflecting surface 60 of mirror 6. The polymerizable media are now polymerized, for instance over a period of 24 hours at room temperature.

If a special design of the terminating stopper 7 is desired, as it may be the case for interstitial applications, then stopper 7, which has been introduced into outer tube 5 prior to polymerization, can be pulled out of outer tube 5. The cavity left by the stopper can then be cleaned and an appropriate metallic or other stopper, for instance a stopper having a sharp tip for interstitial applications, can now be introduced and glued in place as is shown in FIG. 10. In those applications, in which also an axial emission of light is desired, the mirror 6 can be omitted and the metal tip can be replaced with a transparent plastic tip so as to allow for simultaneous axial illumination of the tissue. It is of course possible (as shown in FIG. 10), that the mirror and the stopper can be made out of one part which is sharpened before introduction.

We claim:

1. A process for manufacturing a light diffuser for radial emission of light which has been delivered to the light diffuser in an axial direction, the light diffuser comprising an end face polished at its distal end, a cladding and a core, said core comprising a first end where light enters the core and a second end distal thereto, said process comprising:

removing the cladding in an active region near the distal end of the optical waveguide to expose the core to form an exposed active region;

roughening the exposed active region;

embedding the exposed active region in a first layer of an elastic substance which has a refractive index similar to the refractive index of the cladding and which does not contain any scattering particles;

embedding the first layer of elastic substance with the exposed active region embedded therein into a second layer of an elastic substance, which contains scattering particles; and wrapping an outer tube around the second layer of elastic substance.

2. The process of claim 1 further comprising the steps of:

applying a polymerizable, fluid medium, which is at least partially not yet polymerized to the roughened exposed active region prior to embedding into the first layer of an elastic substance, wherein the medium adhering to the core is then polymerized and thus at least a part of the first layer embedding the exposed active region of the core is produced;

sucking a first polymerizable, fluid medium, which is at least partially not yet polymerized and which does not contain any scattering particles through the distal end of the core into the outer tube and subsequently sucking a second polymerizable fluid medium, which is at least partially not yet polymerized and which contains scattering particles through the distal end of the core into the outer tube;

introducing a terminating stopper at a distal end of the outer tube and subsequently introducing the optical waveguide into the outer tube through a proximal end thereof;

forwarding the active region, which is embedded in the first layer, through the, outer tube until it is located in the second polymerizable fluid medium containing the scattering particles; and allowing the polymerizable media to polymerize.

3. The process of claim 2, wherein prior to the introduction of the terminating stopper a mirror is introduced through the distal end into the outer tube.

4. The process of claim 2 wherein the optical waveguide introduced into the outer tube has a core with a diameter in the range of from about 250 micrometers to about 3000 micrometers.

5. The process of claim 1, wherein a primer is applied to the exposed active region prior to embedding the exposed active region into the first layer of elastic substance.

6. The process of claim 1 wherein the optical waveguide introduced into the outer tube has a core with a diameter in the range of from about 500 micrometers to about 750 micrometers and wherein the outer tube has an inner diameter being 100 micrometers larger than the outer diameter of the core, the outer diameter of the outer tube being in the range from 0.9 mm to about 1.2 mm.

7. The process of claim 1 wherein the length of the exposed active region is up to about 100 mm.

8. The process of claim 1 wherein the optical waveguide is comprised of polymethylmethacrylate; the cladding is comprised of a fluorinated polymer; the first and second layer of elastic substance is comprised of silicone; the scattering particles are $TiO_2$-particles having a diameter of about 200 nm; and the outer tube is comprised of a material selected from the group consisting of polyamide, polytetrafluoroethylene and polypropylene.

9. The process of claim 1 wherein a connector is provided at the first end of the core of the optical waveguide, the connector being connected to a respective counterpart at an assembly for delivering light into the core of the optical waveguide.

* * * * *